United States Patent [19]

Zolman et al.

[11] Patent Number: 5,013,324

[45] Date of Patent: May 7, 1991

[54] PROSTHETIC IMPLANT WITH WRAPPED POROUS SURFACE

[75] Inventors: Arden R. Zolman, Warsaw; Phillip J. Andersen, Silver Lake; Steven T. Bayne, Warsaw, all of Ind.

[73] Assignee: Zimmer, Inc., Warsaw, Ind.

[21] Appl. No.: 277,527

[22] Filed: Nov. 28, 1988

Related U.S. Application Data

[63] Continuation of Ser. No. 88,363, Aug. 24, 1987, abandoned.

[51] Int. Cl.$^5$ .............................................. A61F 2/28
[52] U.S. Cl. .......................................... 623/23; 623/23
[58] Field of Search .................. 623/16, 18, 19, 20, 623/22, 23, 66

[56] References Cited

U.S. PATENT DOCUMENTS

| | | | |
|---|---|---|---|
| D. 283,731 | 5/1986 | Kenna | D24/33 |
| 3,026,610 | 3/1962 | Wakefield | 29/451 |
| 3,605,123 | 9/1971 | Hahn | 3/1 |
| 3,808,606 | 5/1974 | Tronzo | 3/1 |
| 3,855,638 | 12/1974 | Pilliar | 3/1 |
| 3,906,550 | 9/1975 | Rostoker et al. | 3/1.912 |
| 4,064,567 | 12/1977 | Burstein et al. | 623/23 |
| 4,276,765 | 7/1981 | Yoneda | 72/402 |
| 4,406,023 | 9/1983 | Harris | 3/1.912 |
| 4,479,271 | 10/1984 | Bolesky et al. | 3/1.911 |
| 4,495,664 | 1/1985 | Blanquaert | 3/1.913 |
| 4,536,894 | 8/1985 | Balante et al. | 623/23 |
| 4,570,271 | 2/1986 | Sump | 623/18 |
| 4,589,883 | 5/1986 | Kenna | 623/22 |
| 4,608,055 | 8/1986 | Morrey et al. | 623/23 |
| 4,636,219 | 1/1987 | Pratt et al. | 623/22 |
| 4,644,942 | 2/1987 | Sump | 623/16 |
| 4,660,755 | 4/1987 | Farling et al. | 228/178 |
| 4,718,912 | 1/1988 | Crowninshield | 623/23 |
| 4,718,916 | 1/1988 | Morscher | 623/23 |
| 4,728,335 | 3/1988 | Jurgutis | 623/23 |
| 4,752,296 | 6/1988 | Buechel et al. | 623/23 |
| 4,778,475 | 10/1988 | Ranawat et al. | 623/23 |
| 4,828,566 | 5/1989 | Griss | 623/23 |

FOREIGN PATENT DOCUMENTS

| | | |
|---|---|---|
| 0178650 | 4/1986 | European Pat. Off. . |
| 273871 | 7/1988 | European Pat. Off. . |
| 2404214 | 8/1974 | Fed. Rep. of Germany ........ 623/23 |
| 1207495 | 5/1985 | Italy . |
| 2059267 | 4/1981 | United Kingdom . |
| 2142544 | 1/1985 | United Kingdom . |
| 2142830 | 1/1985 | United Kingdom . |
| 2153233 | 8/1985 | United Kingdom . |

OTHER PUBLICATIONS

Zimmer brochure—"Collarles HGP Femoral Prosthesis"—1986.
Howmedica ad—"The PCA Total Hip System"—JBJS, Jun. 1984, 66-A.
Osteonics brochure—"Integrated Systems of Implants and Instrumentation"—1984.
Osteonics brochure—"HS2P Micro-structured Hip System"—1984.
S & G Implants brochure—"Anatomical Hip Endoprosthesis System-Lubeck".
Richards ad—"Opti-Fix Porous Coated Hip System"—JBJS, Feb. 1987, 69-A.
Techmedica ad—"Customize, Don't Compromise"—JBJS, Jan. 1987, 69-A.
Kirschner ad—"Freedom of Choice: A New Dimension in Hip Arthroplasty"—JBJS, Jan. 1987, 69-A.
DePuy ad—"Exclusive . . . The AML Total Hip System"—JBJS, Jan. 1987, 69-A.
Intermedics Orthopedics brochure—"APR Universal Hip System"—1984.
McDonnell Douglas ad illustrating a Techmedica prosthesis—Industry Week, Apr. 1, 1985.

*Primary Examiner*—David J. Isabella
*Attorney, Agent, or Firm*—Margaret L. Geringer

[57] ABSTRACT

A prosthetic implant including a porous pad separate from the stem of the implant and in which the pad is adapted to be wrapped around the stem for attachment thereto. The pad is first precontoured into a preliminary shape and is then wrapped about the stem in a second and final shape corresponding to the shape of the stem portion about which it is wrapped and subsequently secured.

7 Claims, 6 Drawing Sheets

PROSTHETIC IMPLANT WITH WRAPPED POROUS SURFACE

This application is a continuation of application Ser. No. 07/088,363 filed Aug. 24, 1987 now abandoned.

BACKGROUND OF THE INVENTION

The present invention relates to a prosthetic implant device and more particularly to such implants including porous surfaces thereon. This invention is particularly suitable for use as a femoral component for a hip prosthesis, although is not limited thereto.

Heretofore, various types of porous surfaces have been incorporated into prosthetic implants. Such porous implants are often implanted without the use of any type of bone cement material so that the porous surface will be in direct contact with the bone surface. After a period of time, bony ingrowth occurs in and around the porous surface to biologically affix or further secure the implant in the bone. Alternatively, an implant having a porous surface may be implanted with bone cement, such that the penetration of the bone cement into the porous surface of the prosthesis will enhance the fixation of the prosthesis.

The following U.S. patents disclose prosthetic implants which include various types of porous surfaces:

U.S. Pat. No. 3,906,550 to Rostoker et al. discloses a porous fiber metal structure adapted for attachment to a prosthesis. The fiber metal material is molded directly into the desired precise shape using dies and punches.

U.S. Pat. No. 4,479,271 to Bolesky et al. discloses a prosthesis including porous surfaces which are also either molded and compressed directly into shape or compressed and cut directly into shape.

U.S. Pat. No. 4,536,894 to Galante et al. discloses a prosthesis including porous surfaces in which the porous surfaces are porous pads which are compressed and cut directly to the desired shape and then adhered to substantially flat surfaces.

U.S. Pat. No. 4,570,271 to Sump discloses a prosthesis with a porous surface in which the porous coating is preformed directly into the desired shape which corresponds to the preselected surface of the prosthesis. The preform porous coating is then overlaid onto the preselected surface, compressed, and heated to adhere the preform to the prosthesis. The preform may be produced by conventional multi-layer knitting, braiding, winding, weaving, or other continuous wire processes.

U.S. Pat. No. 4,589,883 to Kenna discloses a prosthesis including a porous surface in which the porous coating is comprised of spherical particles which appear to have been directly bonded to the prosthesis stem.

U.S. Pat. No. 4,636,219 to Pratt et al. discloses a prosthesis including a porous surface comprised of a layered metal mesh structure. The mesh may be bonded to a thin substrate (on the order of 0.010 to 0.012 inch) which thin substrate can then be cut or formed and applied to the body of a prosthesis on a flat surface as in FIG. 3 of Pratt et al. or contoured into specific shapes by processes such as creep forming.

U.S. Pat. No. 4,660,755 to Farling et al. discloses a method for constructing a surgial implant in which a porous layer is bonded to a substrate in the absence of a furnace, the bonding occurring via an electrode.

U.K. Patent Application No. GB2059267A to Ducheyne discloses a type of porous metal wire mesh suitable for use on a prosthesis.

U.K. Patent Application No. GB2142830A to Brown et al. discloses a prosthetic implant having a porous surface provided by a perforated micro-contoured sheet.

U.K. Patent Application No. GB2153233A to Lee et al. discloses a prosthetic implant which utilizes wedges to wedge between the bone cavity wall and the prosthesis stem in which the wedges may include a porous surface.

European Patent Application No. EP0178650A2 to Ducheyne discloses a porous flexible metal fiber material for implantation in conjunction with a prosthesis in which one or more layers of the porous sheet material are pressed against the bone surface with a layer of bone cement then between the implant and the porous sheet material.

OBJECTS AND SUMMARY OF THE INVENTION

A principle object of this invention is to provide a prosthetic implant which includes a porous pad separate from the prosthesis stem which is adapted for wrapping around the stem for attachment thereto.

Another object of the invention is to provide a prosthetic implant which includes a porous pad separate from the fixation surface base portion such that the porous pad has a first preliminary precontoured shape. The porous pad is adapted for wrapping about the fixation surface base portion in a second and final shape corresponding to the shape of the fixation surface base portion about which it is wrapped.

A further object of the invention is to provide such a prosthetic implant in which the pad is wrapped about at least two adjacent sides A still further object of the invention is to provide a process for wrapping a porous pad about a prosthesis stem in which the pad has a first preliminary, substantially flat precoutured shape which is subsequently wrapped about the stem into a second and final shape for attachment to the stem.

The present invention accomplishes the above objects and as such provides a prosthetic implant which includes a porous pad which is preliminarily formed into a first shape and then wrapped and/or formed about the stem of the implant to conform to the shape of the implant in a second and final shape. The pad is then adhered to the stem. The invention also provides a process for preparing the porous pad and for conveniently wrapping the pad about the stem.

BRIEF DESCRIPTION OF THE DRAWINGS

These features and objects of the invention, as well as others, will become apparent to those skilled in the art by referring to the accompanying drawings.

DETAILED DESCRIPTION OF THE INVENTION

Figure 1:
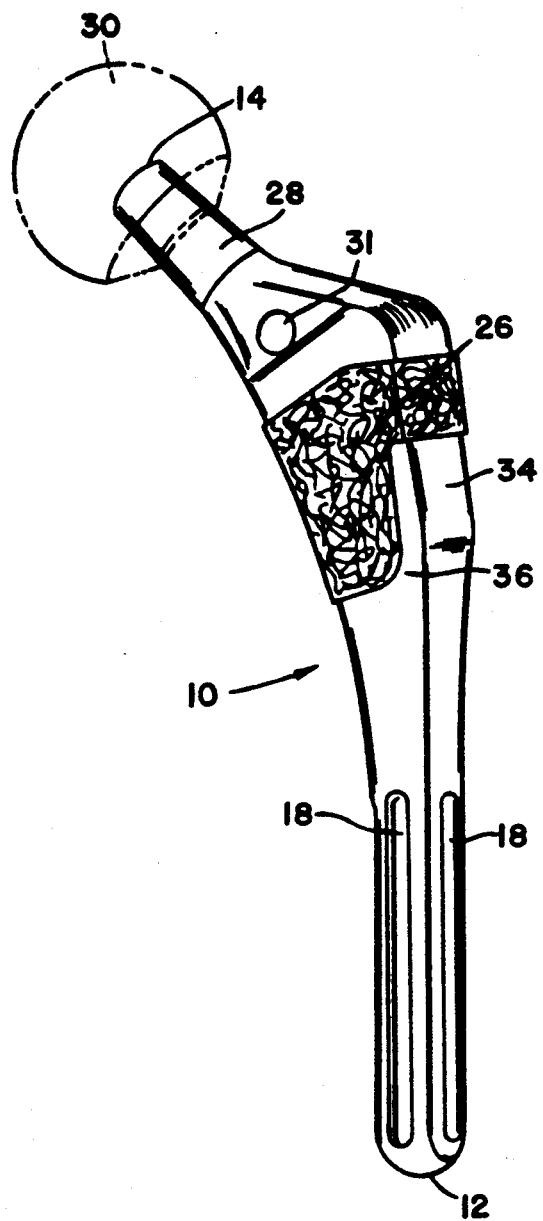
FIG. 1 is a perspective view of a femoral component for a hip prosthesis according to the present invention.

FIGS. 1-13 illustrate a particularly advantageous embodiment of a prosthetic implant according to the present invention. The invention will be described with reference to a femoral component 10 of a hip prosthesis and is particularly suitable as such. However, it is understood that the principles of the invention may be suitable for other implants having elongated fixation stems. In addition, it is noted for reference that the particular femoral component 10 described herein is designed for implantation in a right femur, while a corresponding femoral component (not shown) for implantation in a left femur would be a mirror image of the femoral component 10 shown for the right femur.

The femoral component 10 of FIGS. 1-6 includes a distal end 12 and a proximal end 14. As is well known, the femoral component 10 is intended to fit within the intramedullary canal of a femur (not shown) such that the proximal end extends outwardly from the intramedullary canal of the femur to cooperate with an acetabulum or acetabular prosthetic member via a ball or the like carried at the proximal end 14. A distal portion 16 may include a plurality of grooves 18 extending longitudinally. A proximal portion 24 includes a porous surface or pad 26 encircling the femoral component 10. The distal portion 16 and the proximal portion 24 comprise the stem portion 20 of the femoral component 10. A neck 28 extends from the proximal portion 24 and is adapted to carry a ball 30 shown in phantom lines in FIG. 1. An aperture 31 adjacent the neck 28 accommodates a tool for removing the femoral component 10 from the intramedullary canal should removal be necessary. The porous pad 26 is designed to extend outwardly from the proximal portion 24 albeit a small extension of about 0.5 mm past the adjacent smooth surface of the proximal portion 24.

Figure 2:
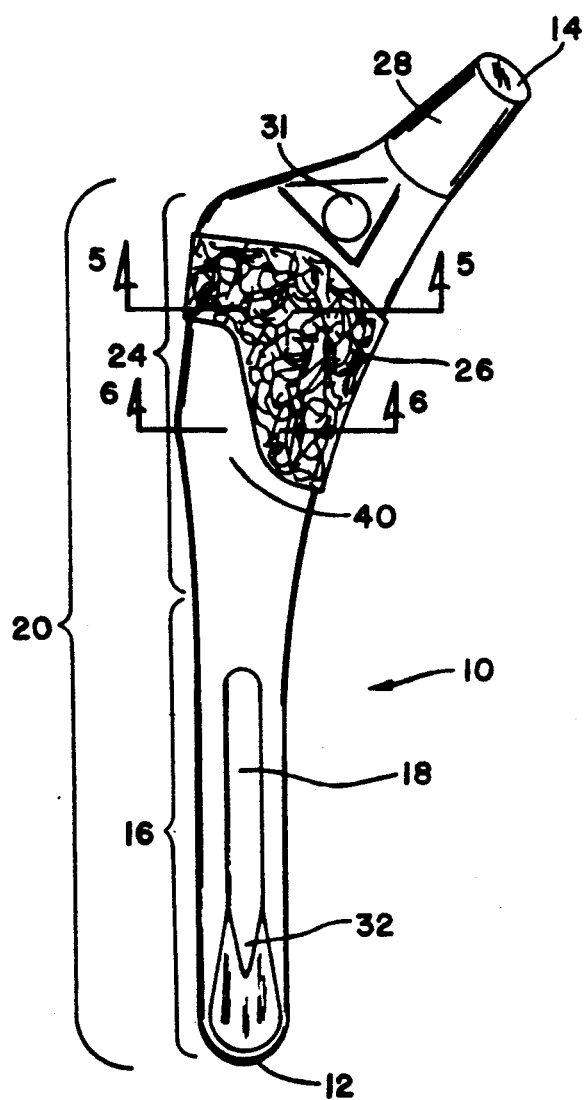
FIG. 2 is an anterior side elevational view thereof.
Figure 3:
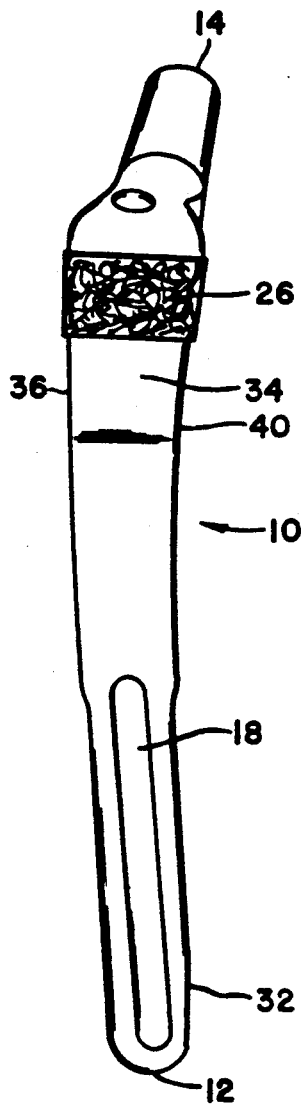
FIG. 3 is a lateral side elevational view thereof.
Figure 4:
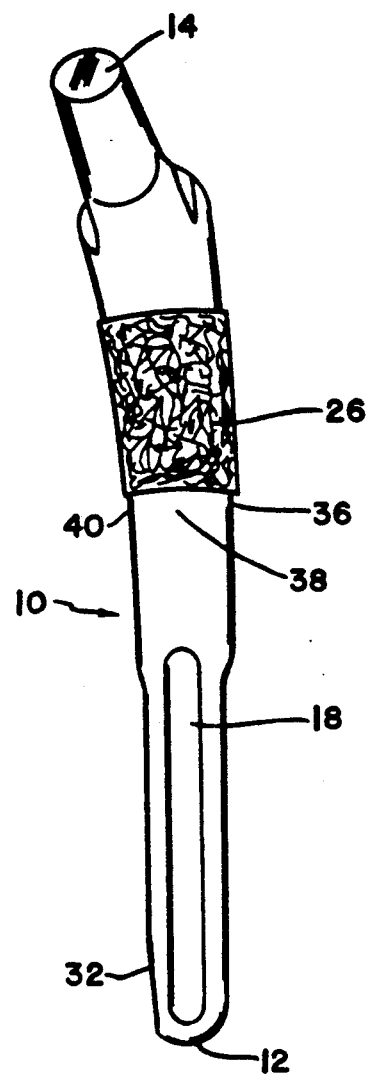
FIG. 4 is a medial side elevational view thereof.

FIGS. 2, 3, and 4 illustrate a chamfer 32 on the anterior side of the femoral component which may be included to avoid impingement of the distal end 12 into the bone surrounding the intramedullary canal at that location.

As shown in FIGS. 1-4, the proximal portion 24 includes a lateral side 34, a posterior side 36, a medial side 38, and an anterior side 40. A porous pad 26, as shown in the embodiment of FIGS. 1-6, is circumferentially wrapped around the proximal portion 24 of the stem portion 20. The pad 26 may be formed of any suitable porous material that is adapted to be preliminarily pressed into a first shape and then subsequently wrapped about the stem portion 20 into a second shape conforming to the shape of the stem portion 20. One such suitable material is the fiber metal structure disclosed in U.S. Pat. No. 3,906,550 to Rostoker and Galante, although it is noted that the Rostoker et al. patent teaches that the fiber metal material is molded directly into the desired shape, rather than providing a first preliminary shape which is then subsequently wrapped or formed about a prosthetic implant into the second and final shape in accordance with the present invention. It is understood that any suitable porous material, particularly fibrous (wire-type) porous structures which are adaptable to be practiced in accordance with the present invention, may be utilized. The material for the porous pad may be titanium wire having a diameter of 0.010 inches, and the material for the femoral component may also be titanium. Again it is understood that any suitable materials may be utilized.

Figure 9:
FIG. 9 is a top view of a pressed and prebonded sheet of porous material.
Figure 10:
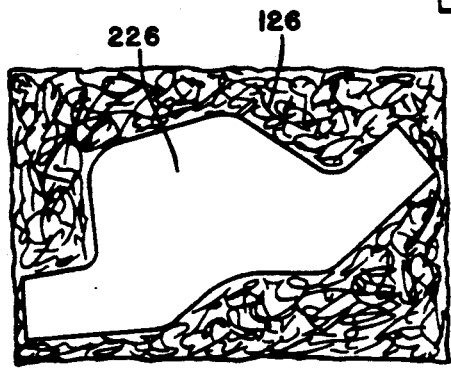
FIG. 10 is a top view of the sheet of FIG. 9 illustrating a cut out portion.
Figure 11:
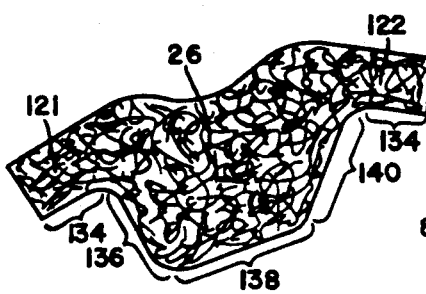
FIG. 11 is a top view of the porous pad formed from the cut out of FIG. 10.

The shape of the porous pad 26 may have any desirable configuration, although preferably the pad is first formed in or pressed into a substantially flat sheet 126 (see FIGS. 9-11). The outer boundary of the pad 26 may have any suitable contour. The porous pad 26 is separate from the stem portion 20. The pad 26 is adapted for wrapping around the stem portion 20 for attachment thereto. The porous pad 26 has a first preliminary precontoured shape as shown in FIG. 11 and is then subsequently wrapped and/or formed about the stem portion 20 for attachment thereto in a second and final shape corresponding to the shape of the stem portion 20 as shown in FIGS. 1-4. The porous pad 26 is wrapped around at least two to three adjacent sides, although preferably is wrapped around all four sides 34, 36, 38, and 40 to form a continuous porous surface circumferentially about the stem portion 20.

The porous material, such as a kinked titanium fiber metal, is press formed into a sheet 126 of porous material. The sheet 126 may have any desired thickness or dimensions. The dimensions of the sheet 126 may be adapted to cut out a single pad 26 having a desired outer boundary or adapted to cut out multiple pads 26 from a single sheet. The sheet 126 is prebonded in a vacuum furnace by holding the sheet for a suitable length of time at a temperature sufficient to create metallurgical bonds at the points of contact of the fibers of the porous material within the sheet 126. A porous pad 26 having the desired outer contour is then cut from the sheet leaving a corresponding cut out 226 in the sheet 126. Prebonding the fiber metal sheet prior to cutting it creates mechanical integrity in the sheet 126 so that the fiber material is more easily formable and holds its shape better.

The porous pad 26, shown in FIG. 11 which is subsequently applied to the femoral component 10 of FIGS. 1-4, includes a medial pad side 138 to correspond to the medial stem side 38, posterior and anterior pad sides 136 and 140 each extending from or adjacent to the medial pad side 138 and adapted to correspond to the posterior and anterior stem sides 36 and 40, respectively, and first and second tabs 121 and 122 extending from the posterior and anterior sides, respectively. The two tabs together comprise the lateral pad side 134 which will correspond to the lateral stem side 34 of the femoral component 10. The pad 26 may be asymmetric as shown with the posterior porous pad surface 136 having greater surface area than the anterior porous pad surface 140 and with the medial pad surface 138 being longer than the lateral pad surface 134. However, the pad 26 could readily be made symmetrically, if desired, as any appropriate shape may be utilized for the pad 26.

Figure 5:
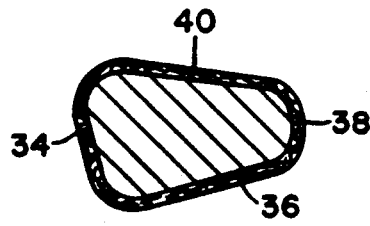
FIG. 5 is a cross-sectional view taken along line 5—5 of FIG. 2.
Figure 6:
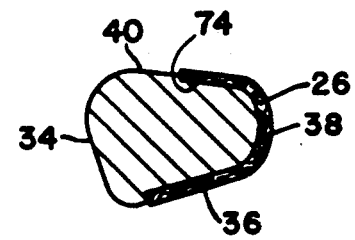
FIG. 6 is a cross-sectional view taken along lines 6—6 of FIG. 2.

The pad 26 is then ready to be wrapped about the stem portion 20. The proximal portion 24 of the stem portion 20 includes a recess 74 (see FIG. 6) having a shape corresponding to the pad 26 and adapted to receive the pad 26 for subsequent attachment thereto. The pads 26 can be shaped to conform to any desirable and suitable implant stem or fixation surface configuration. The proximal portion 24 of the stem portion 20 of the femoral component shown has an asymmetric noncircular cross-section as shown in FIGS. 5 and 6.

Figure 7:
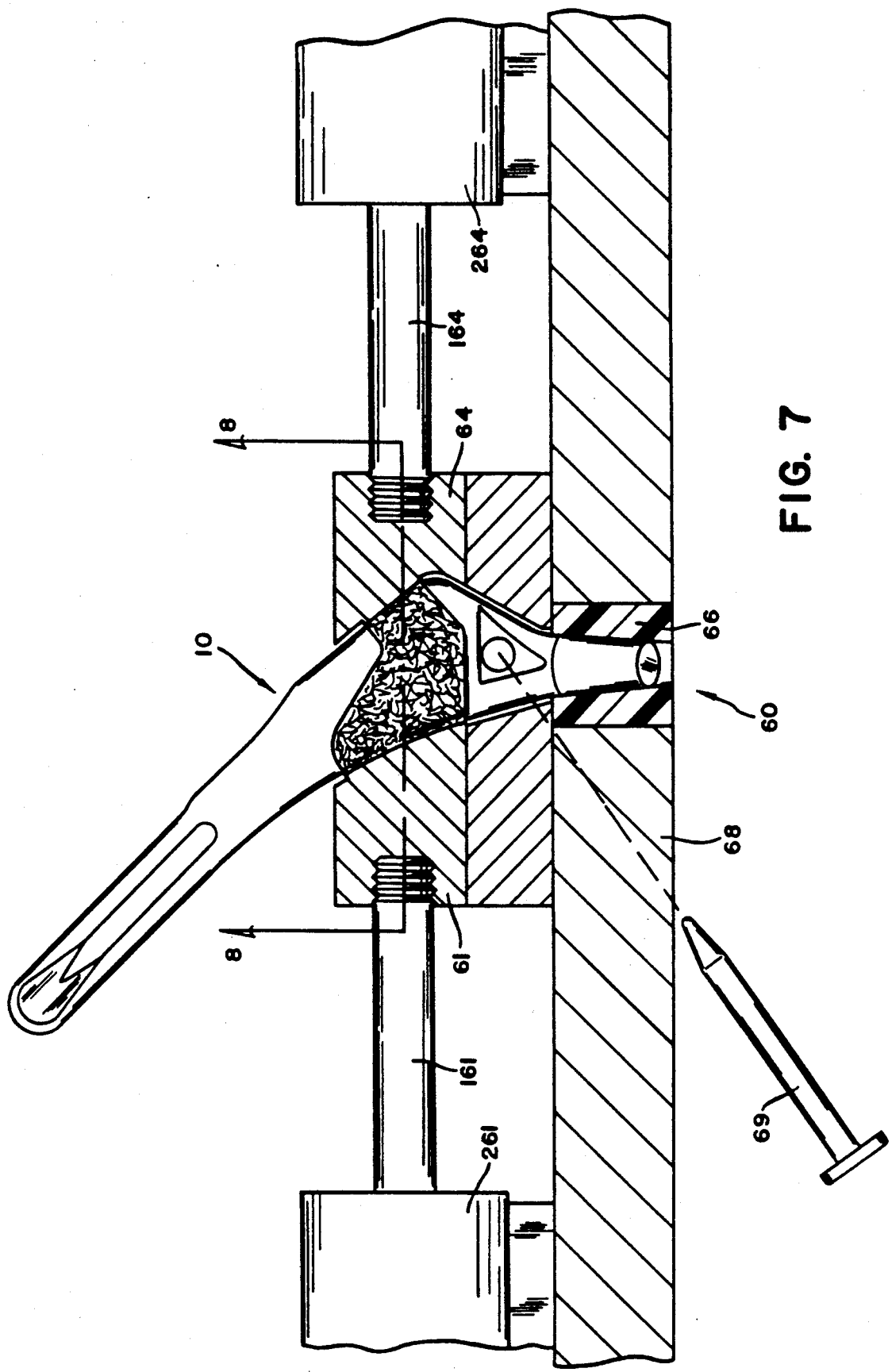
FIG. 7 is a side view of a femoral component according to the present invention located in a forming fixture with the fixture shown in a cross-sectional view taken along lines 7—7 of FIG. 8c.
Figure 8B:
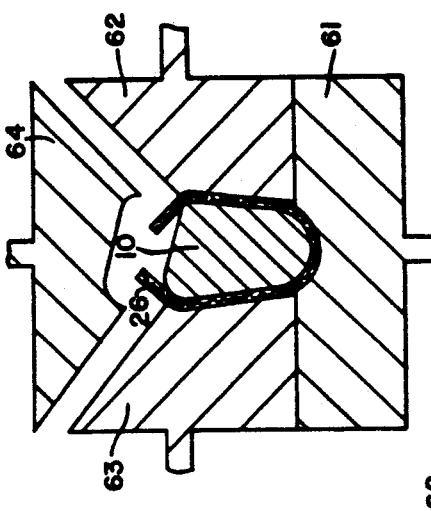
FIGS. 8a, 8b, and 8c are cross-sectional views taken along lines 8—8 of FIG. 7 of the forming fixture illustrating various jaws in activated positions about the femoral component stem.
Figure 8C:
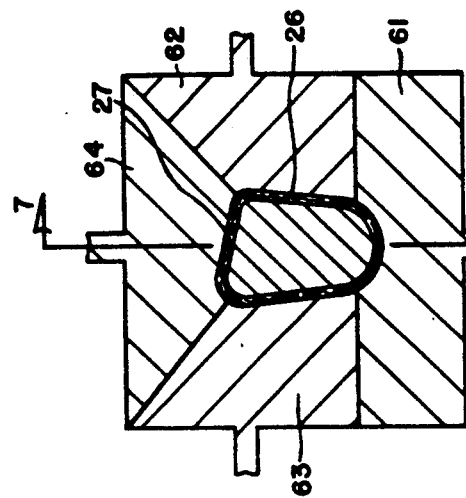
Figure 8:
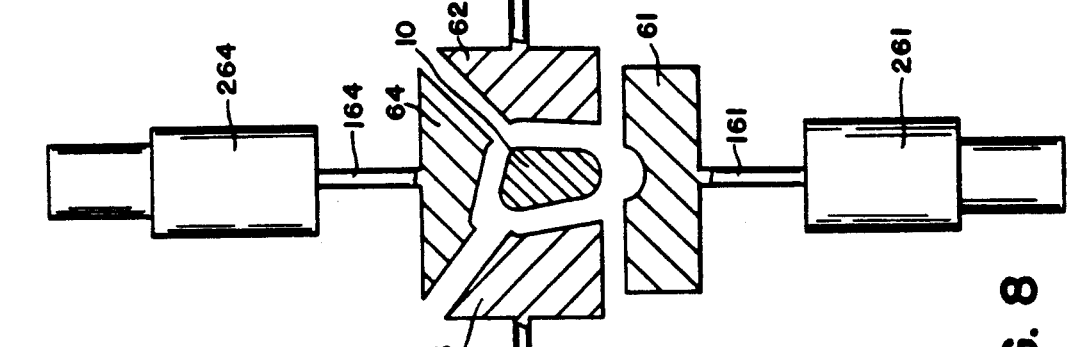
FIG. 8 is a cross-sectional view of the forming fixture taken along lines 8—8 of FIG. 7.

The process for wrapping the porous pad 26 may be accomplished by placing the femoral component 10 (without pad 26) in a forming fixture 60 as shown in FIGS. 7 and 8. The fixture 60 has a plurality of forming jaws 61, 62, 63, and 64. The forming jaws are each operated by corresponding rod 161, 162, 163, and 164, respectively, which operatively connects the jaws to cylinders 261, 262, 263, and 264, respectively. The cylinders 261, 262, 263, and 264 may be air operated cylinders or hydraulic cylinders or any other suitable activation mechanism. The jaws, rods, and cylinders may be made of tool steel, or any other suitable material strong enough to form the porous pad 26 about the femoral component 10.

The neck 28 of the femoral component 10 is seated in a cylindrical bushing 66 within base plate 68 of fixture 60 to hold the femoral component 10 in place. A sliding location pin 69 may be placed through the aperture 31 to keep the femoral component 10 from rotating while the forming is taking place. The bushing 66 may suitably be made from a nonmetallic material such as delrin so as not to scratch the neck 28. The base plate may be made of aluminum or steel. Other suitable means of holding the femoral component 10 securely in the forming fixture 60 could also be utilized.

Figure 8A:
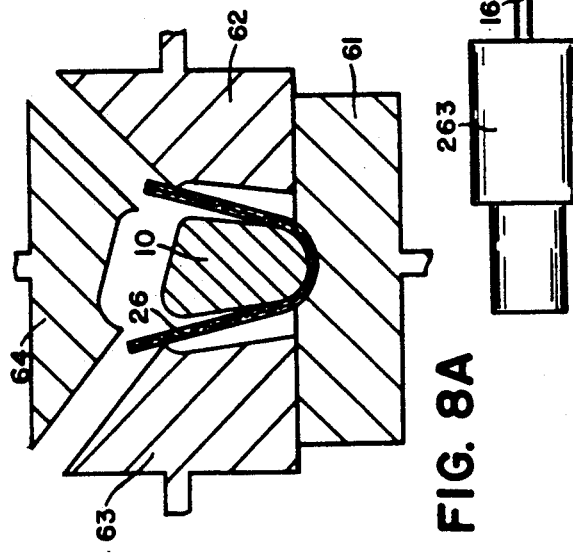

The jaws 61, 62, 63, and 64 are each in a retracted position about the femoral component 10. The precut substantially flat porous pad 26 is placed in position between the jaws and the implant 10 with the medial pad portion 138 aligned with the corresponding medial side 38 of the stem portion 20. The jaws, which have interfacing surfaces corresponding to the desired pad and stem configuration, are then activated in a predetermined sequence to form the pad 26 about the implant conforming the pad 26 to the shape of the implant 10 as shown in FIGS. 8a, 8b, and 8c. In FIG. 8a the first forming jaw 61 is activated from its retracted position to a position in which the first jaw 61 is pressed up against the medial porous pad surface 138 which is thus pressed against the corresponding medial side 38 of the stem portion 20 shaping and locating the respective portion of th pad 26 thereto. The first jaw 61 is then held in its activated position against the stem portion 20.

Alternatively, the medial porous pad surface 138 could be preformed to the shape of the medial side 38 by utilizing a correspondingly shaped separate forming dye (not shown) for just the medial side (rather than forming this medial side using the sequential fixture 60). The separate dye would include a substantially U-shaped depression such as that shown in the cross-section of jaw 61 in FIG. 8a and a corresponding U-shaped projection corresponding to the outer contour of the medial side of the femoral component, which when brought together with the pad 26 in between would preform the pad 26 into the substantially U-shaped configuration, such as that achieved using the first jaw 61 of the sequential forming fixture 60. If such a separate dye is used, the pad 26 having the preformed (U-shaped) medial pad surface 138 would then be placed in position in the forming fixture 60 between the jaws and the implant 10 with the preformed medial pad 138 aligned with the medial side 38 of the stem portion 20. The jaw 61 would be activated to hold the pad 26 having the preformed medial pad surface against the stem portion 20. The remaining sequential activation of the jaws would then continue.

The second and third jaws 62 and 63 may be then activated simultaneously as shown in FIG. 8b to press the posterior and anterior porous pad surfaces 136 and 140, respectively, against the posterior and anterior sides 36 and 40 of the stem portion 20 thus shaping the respective portions of the pad thereto. Jaws 61, 62, and 63 are then held in this activated position against the stem portion 20.

The fourth jaw 64 is then activated as shown in FIG. 8c to press the first and second tabs 121 and 122 of the lateral porous pad surface 134 against the lateral side 34 of the stem portion 20 thus shaping the respective portions of the pad thereto. The tabs 120 and 122 mate together on the lateral side 34 to form a flush interface 27, thus providing a continuous circumferential porous surface connecting the anterior, medial, posterior, and lateral sides.

The forming jaws are then released from their activated positions, and thus retracted away from the stem portion 20. The femoral component 10 with the conformed pad 26 surrounding it is removed from the forming fixture 60. The femoral component 10 is then placed in an appropriate bonding fixture 80 such as in FIGS. 12-13 in which the porous pad is held securely in place against the stem portion 20. The pad 26 is positioned securely in the recess 74 which corresponds to the wrapped shape of the pad 26. The porous pad 26 is then bonded to the stem portion 20 to securely attach it thereto. The bonding may be achieved by diffusion bonding the pad to the stem portion by holding the pad securely thereagainst at a sufficient temperature for a sufficient length of time to achieve secure bonding. However, it is understood that other bonding processes such as sintering or other suitable bonding methods may be utilized.

Figure 12:
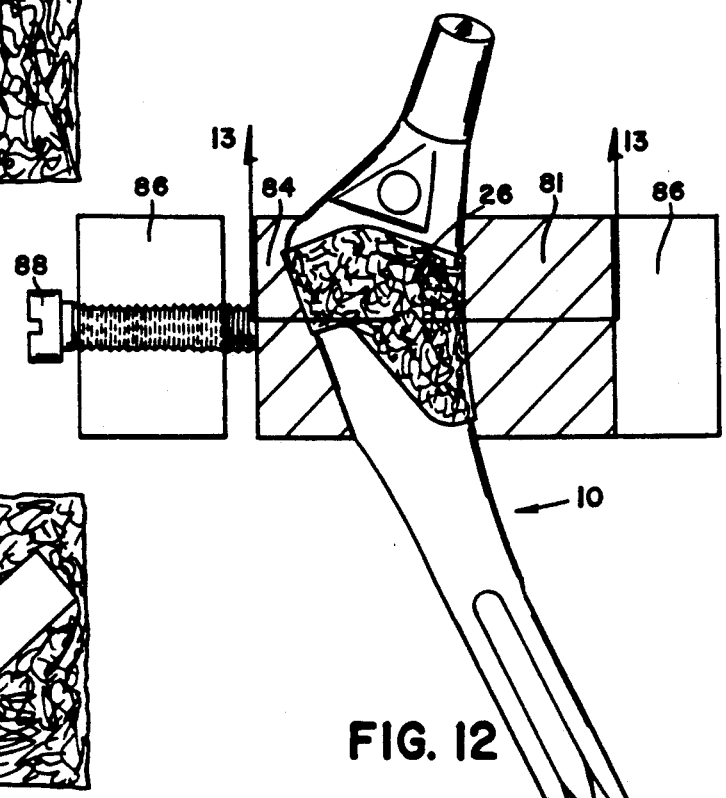
FIG. 12 is a side view of a femoral component according to the present invention located in a bonding fixture with the fixture shown in a cross-sectional view taken along lines 12—12 of FIG. 13.
Figure 13:
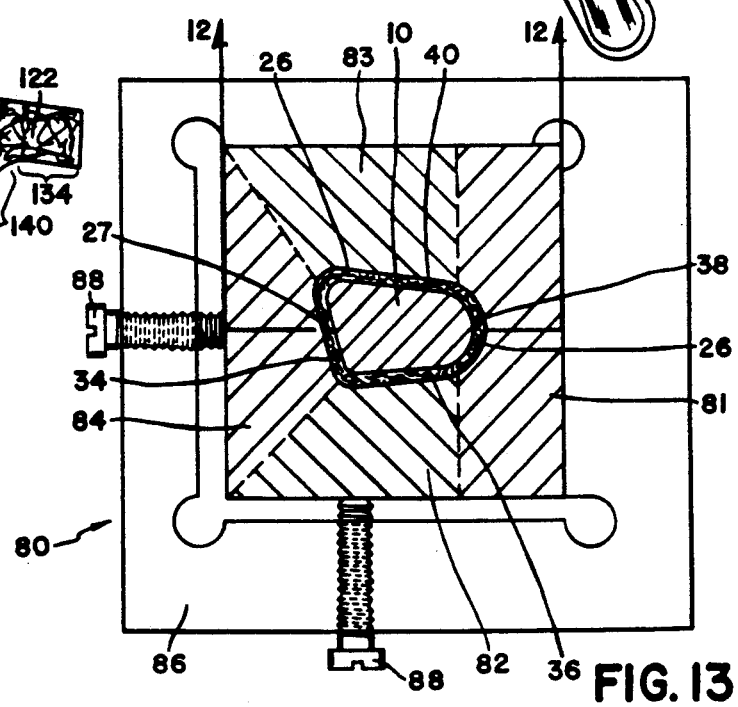
FIG. 13 is a cross-sectional view of the bonding fixture taken along lines 13—13 of FIG. 12.

Although any appropriate bonding fixture or holding mechanism may be used for bonding the pad 26 to the stem portion 20, FIGS. 12 and 13 illustrate such a suitable fixture 80. The fixture 80 includes a support frame 86 with a plurality of holding or bonding locks or jaws 81, 82, 83, and 84 which surround the porous pad 26 on the proximal portion 26 and which conform to the shape of the stem portion 20 about which they are positioned. The bonding blocks which hold the pad 26 in place against the stem portion 20 are suitably made of a carbon material, as is the frame 86. The bonding blocks 81, 82, 83, and 84 are placed under sufficient pressure evenly holding the pad 26 against the stem portion 20 via screws 88.

Alternatively, rather than forming the substantially flat first preliminarily shaped pad 26 about the stem portion 20 into its second and final contoured shape, the pad 26 can be formed about a mandrel (not shown) which has a shape which corresponds to the portion of the implant to which the pad is to be attached. This forming about a mandrel can be done with a fixture 60 such as that described above used for forming the substantially flat or medially preformed pad 26 about the implant itself. Then the formed pad 26 which has been shaped about the mandrel is removed from the mandrel and placed about the femoral component 10. The pad 26 can then be securely bonded to the stem portion 20 as described above.

Figure 14:
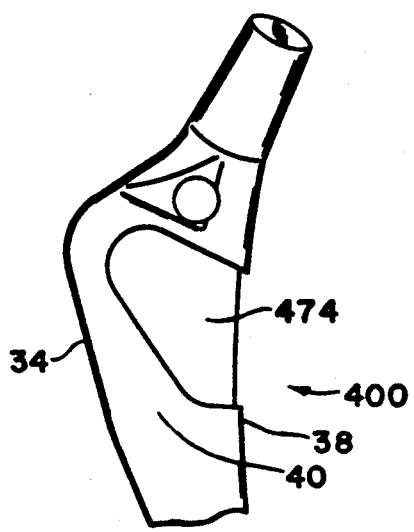
FIG. 14 is an anterior side elevational view of an alternate embodiment of a femoral component.
Figure 15:
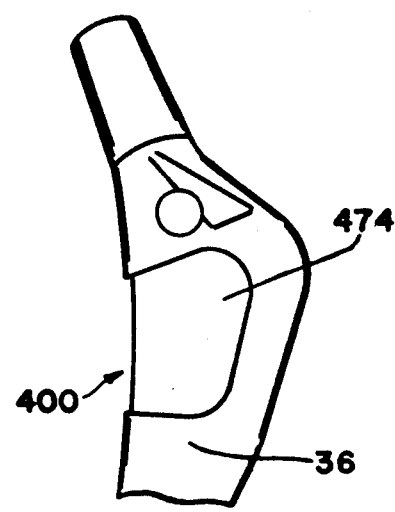
FIG. 15 is posterior side view of the component of FIG. 14.
Figure 16:
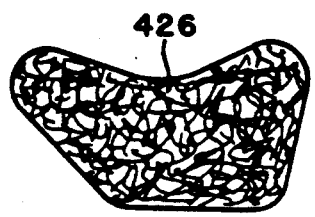
FIG. 16 is an alternate embodiment for a porous pad to be used in conjunction with the component of FIG. 14.

An alternate embodiment for a femoral component 400 is shown in FIGS. 14-16 in which the porous pad 426 is adapted to fit in recess 474. FIGS. 14 and 15 show the component 400 without the porous pad 426 thereabout. The pad 426 is adapted to be wrapped about three adjacent sides including the lateral, medial, and anterior sides 36, 38, and 40 to form a continuous porous surface interconnecting these three sides. Since the pad 426 does not completely surround all sides of the implant, the pad 426 may be conveniently formed from its substantially flat first preliminary shape (as shown in FIG. 16) to its second and final contoured shape which corresponds to the shape of the recess 474 in the stem portion 20 either by using a correspondingly shaped (substantially U-shaped for the embodiment shown in FIGS. 14-16) separated single forming dye (not shown), or a forming fixture 60 with multiple sequentially operated forming jaws such as previously described. The formed pad 426 can then be bonded to the stem portion 20 in a similar manner as previously described for the pad 26 which circumferentially surrounds the stem portion.

The prosthetic implant of the present invention provides an implant having a wrapped porous pad and a method of wrapping such pad about a prosthetic stem portion. The present invention provides for a substantially flat pad having a predetermined outer boundary to be subsequently wrapped about a prosthesis stem to conform to the shape of the stem and to be attached thereto. While this invention has been described and exemplified in terms of particularly advantageous embodiments, those skilled in the art can appreciate that modifications can be made without departing from the spirit and scope of this invention.

We claim:

1. A prosthetic implant including a stem portion having a plurality of sides and a discrete, circumferential porous pad mounted directly on said stem portion in surrounding relation thereto, the pad includes a first end and a second end such that when the pad is mounted on the stem portion, the first end and the second end face each other and are flush with one another without interruption therebetween on one of said sides of the stem portion, and wherein the porous pad is attached securely and directly to the stem portion prior to implantation.

2. The prosthetic implant of claim 1 wherein the stem portion includes a medial side and an oppositely located lateral side interconnected by connecting sides therebetween, and wherein the flush first and second ends are located on the lateral side.

3. The prosthetic implant of claim 1 wherein the porous pad is formed substantially wholly of a fiber metal material.

4. The prosthetic implant of claim 1 wherein the stem portion further includes a recess corresponding to the shape of the porous pad, and wherein the pad is positioned in the recess when attached to the stem portion.

5. The prosthetic implant of claim 1 wherein the implant is a femoral component for a hip prosthesis and the stem portion of the femoral component has a proximal portion and a distal portion and wherein the stem portion further includes a medial, a posterior, an anterior, and a lateral side.

6. The femoral component of claim 5 wherein the porous pad is located substantially in the proximal portion of the hip prosthesis and wherein the proximal portion has a noncircular, cross-sectional configuration.

7. The prosthetic implant of claim 1 wherein the stem portion and the porous pad are both made of metallic materials and the attachment of the pad to the stem portion is achieved by metallurgical bonding therebetween.

* * * * *